United States Patent [19]
Zumschlinge

[11] Patent Number: 6,077,248
[45] Date of Patent: Jun. 20, 2000

[54] MEDICAL PUNCTURING SET

[76] Inventor: Rolf Zumschlinge, An der Isar 3, Pullach 82049, Germany

[21] Appl. No.: 09/007,547

[22] Filed: Jan. 15, 1998

[30] Foreign Application Priority Data

Jan. 17, 1997 [DE] Germany ............ 197 01 546

[51] Int. Cl.[7] .................................................. A61M 5/178
[52] U.S. Cl. .................... 604/169; 604/272; 604/165
[58] Field of Search ........................ 604/169, 164, 604/165, 167, 168, 96, 915, 272, 273, 264; 606/167, 184, 185

[56] References Cited

U.S. PATENT DOCUMENTS

| | | |
|---|---|---|
| 3,727,613 | 4/1973 | Sorenson . |
| 3,952,742 | 4/1976 | Taylor . |
| 4,019,039 | 4/1977 | Anderson . |
| 4,447,235 | 5/1984 | Clarke . |
| 4,496,348 | 1/1985 | Genese . |
| 5,376,075 | 12/1994 | Haughton . |
| 5,531,694 | 7/1996 | Clemens et al. ............... 604/110 |
| 5,562,629 | 10/1996 | Haughton et al. ............... 604/158 |
| 5,697,914 | 12/1997 | Brimhall ............... 604/177 |

FOREIGN PATENT DOCUMENTS

| | | |
|---|---|---|
| 2353641 | 12/1976 | Germany . |
| 3147609A1 | 6/1983 | Germany . |
| 8603357 U | 7/1986 | Germany . |
| 4434567A1 | 4/1995 | Germany . |
| 123520 | 9/1919 | United Kingdom . |

*Primary Examiner*—Ronald Stright, Jr.
*Assistant Examiner*—Jeremy Thissell
*Attorney, Agent, or Firm*—Townsend and Townsend and Crew LLP

[57] ABSTRACT

A puncturing set has a housing with a hose extension. A tubular puncturing needle is disposed inside the housing and extends axially substantially over the length of the hose extension. The needle is movable between an extended position, in which its forward, pointed end projects axially from a free end of the hose extension, and a retracted position, in which the pointed end of the needle is inside the hose extension. At the aft, downstream end of the puncturing needle is a fluid withdrawal mechanism and there is a sealing arrangement between the puncturing needle and the housing.

7 Claims, 2 Drawing Sheets

MEDICAL PUNCTURING SET

BACKGROUND OF THE INVENTION

The present invention relates to puncturing sets such as are generally used in the healthcare field and in particular for the puncturing of pathological, liquid-filled body cavities.

Such puncturing sets are used to collect and remove undesirable liquid accumulations from body cavities or for extracting body fluid samples for diagnostic purposes. It is conventional to use hollow needles, such as cannulas or trocars, which pierce through the surrounding body wall to reach the body cavity that is to be evacuated. Following puncturing, the liquid is withdrawn through the hollow needle. It is a disadvantage of such known arrangements that the needle, which remains in the body cavity while the liquid is withdrawn, can injure the body tissue that surrounds the hollow space.

The use of so-called "Braunülen" for puncturing is also known. A Braunüle is a piercing instrument which has a hollow needle disposed inside a cannula-like plastic tube. The pointed end of the needle extends beyond the forward end of the plastic tubing. A Braunüle is conventionally introduced into the body, for example into a vein, by piercing the body wall with the hollow needle and by then pushing the plastic tubing as far as needed into the body. The needle is then pulled out of the plastic tubing and removed so that the plastic tubing remains in the body, for example in the vein, for connection to an infusion system, for example. The use of Braunülen for puncturing has the disadvantage that the portion of the plastic tubing that remains in the body cavity during the withdrawal of the body fluid can become pinched due to body movements, or moving body organs. When this is encountered, the further withdrawal of liquid can become difficult or impossible.

The above two discussed puncturing methods are particularly in use in connection with so-called "Pleuroergussen", i.e. liquid accumulations in the body cavity surrounding the lung. Here it is necessary to prevent the pointed needle end from injuring the lung as it moves during normal breathing and, over the longer term, assure a reliable removal of even large liquid accumulations.

SUMMARY OF THE INVENTION

It is therefore an object of the present invention to provide a puncturing set for reliably withdrawing liquids from body cavities without undesirably injuring the surrounding body tissue.

A puncturing set constructed in accordance with the present invention has a housing fitted with a flexible, tubular hose extension. A tubular puncturing needle is disposed in and extends axially over substantially the length of the hose extension. The needle is axially movable between an extended position in which a forward, pointed, intake end of the needle projects from the free end of the hose extension, and a retracted position in which the pointed end is disposed inside the hose extension. The rearwardly located, outlet end of the puncturing needle is coupled to a fluid withdrawal mechanism and a sealing arrangement is placed between the needle and the housing.

In the puncturing set of the present invention, the axially movable puncturing needle fulfills two tasks. The first is to pierce through the body wall when the puncturing set is placed in position. The second is to stabilize the hose extension during the withdrawal of liquid to prevent it from becoming pinched. During this phase, the needle is retracted sufficiently far into the hose extension that its pointed end no longer protrudes from the forward end of the hose. As a result, there is no danger that body tissue will be injured during the removal of liquid. A sealing arrangement is provided to prevent ambient air from flowing through an annular channel formed between the puncturing needle and an inner side of the hose extension to prevent an impairment of the liquid withdrawal.

In a particularly advantageous embodiment of the present invention, the sealing arrangement is defined by an inner sealing section formed about the circumference of the puncturing needle and an outer sealing section which is formed on an inside of the housing. The sealing sections are arranged so that they are axially spaced apart when the puncturing needle is in its extended position. In this embodiment, a seal is formed only when the puncturing needle is moved into its retracted position.

In a further, advantageous embodiment of the invention the inner sealing sector is defined by a conical sealing body which is placed about the circumference of the puncturing needle and defines a sealing surface that is obliquely inclined relative to the needle axis. A base of the conical sealing body faces in the direction towards the pointed end of the puncturing needle. The outer sealing section forms an inwardly facing conical surface in the housing. This assures a particularly reliable seal. It is further preferred that at least one of the two cone surfaces has a spherically convex shape.

Another advantageous embodiment of the invention forms the inner sealing section as a spherical sealing body which is placed over the circumference of the puncturing needle. In this embodiment of the invention, the outer sealing section forms a partially spherical inner surface of a hollow space in the housing. In this embodiment, a reliable seal is formed by advancing the spherical sealing body into the partially spherically formed hollow space of the housing.

A particularly preferred embodiment of the present invention enables a locking of the needle in its retracted position. This prevents an unintentional movement of the needle into its extended position, thereby assuring that the pointed end of the needle remains within the hose extension.

It is particularly advantageous when the locking mechanism is constructed as a combined sealing and ratchet arrangement, because this assures a simple and effective locking of the retracted needle.

In a preferred embodiment, the aft end of the needle is axially immovably fixed to a yoke-like cap. A thread, or a thread-like arrangement, connects the cap to the housing. This permits a reliable movement of the needle into its retracted position by rotating the cap relative to the housing. Markings can be applied to the housing and the cap to indicate the relative position of the needle.

Alternatively, an outer thread can be applied to the needle. The housing then has an inner thread for engaging the thread on the needle.

In another embodiment, the wall of the hose extension has radially oriented openings in the vicinity of the free end of the hose. These openings permit a reliable removal of the liquid even if, for example, the front end of the hose extension becomes plugged by tissue particles or the like.

In a further embodiment of the invention, the puncturing is securely held in place while it extends into the body cavity. This is achieved with a radially outwardly expandable wall segment on the exterior of the forward end of the hose extension. A pressure channel extends longitudinally through the wall of the hose extension and communicates with a pressure connection in the aft portion of the housing.

By pressurizing the flexible wall segment with a fluid through the pressure channel, the wall segment becomes inflated, expands itself and, therefore, prevents the unintentional removal of the needle through the body wall through which it was initially inserted. The puncturing set is removed by simply releasing the pressurized fluid in the expandable wall segment of the hose extension. This causes the flexible wall segment to retract itself to an outer diameter which is substantially equal to the outer diameter of the hose extension.

When the aft end of the needle extends into a housing chamber that is fluidly coupled to the fluid withdrawal mechanism, the latter can be mounted directly on the housing.

The withdrawal of fluid from a body cavity by means of a syringe or suction pump is possible by including a three-way valve in the fluid withdrawal mechanism. A first port of the valve is for connection to the syringe or pump, while a hose connects a second exit port of the valve with a fluid collection container. In this manner, the fluid can be sucked from the body cavity with the syringe, and by turning the three-way valve, the fluid can be forced from the syringe into the collection container. This speeds up the emptying of the body cavity because it eliminates the need to constantly reattach the syringe during the removal of the liquid.

It is further advantageous to provide a sight window in the housing or in the rear portion of the puncturing needle. With such a sight window one can determine when, after the initial penetration of the puncturing set into the body cavity, it has reached the liquid pool or accumulation that is to be removed, because at that point liquid begins to flow through either the needle, or laterally of the needle through the hose extension, into the housing, where it becomes visible through the sight window.

BRIEF DESCRIPTION OF THE INVENTION

The invention is further explained by way of an example and with reference to the following drawings.

DESCRIPTION OF THE PREFERRED EMBODIMENTS

Figure 1:
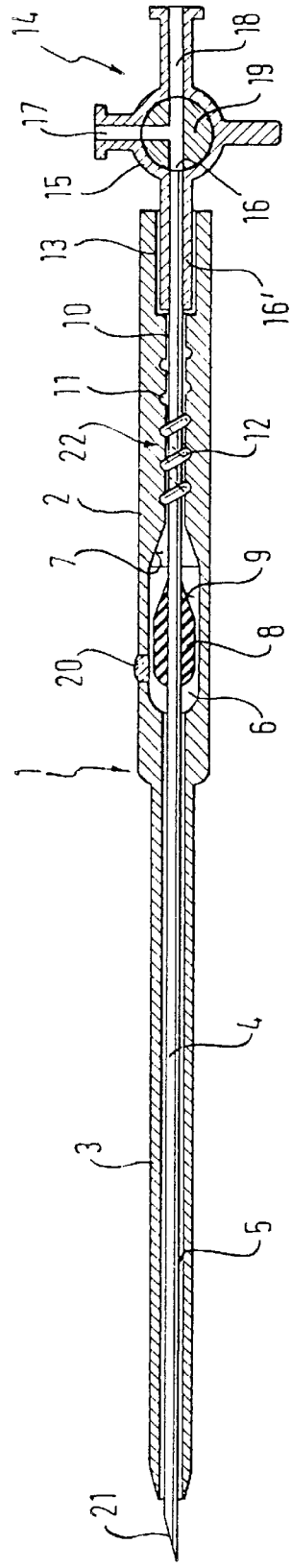
FIG. 1 shows a puncturing set constructed in accordance with a first embodiment of the invention and with its puncturing needle in the extended position.

FIG. 1 shows a puncturing set constructed in accordance with the invention. It has a housing 1 with an aft, enlarged housing segment 2 and a forward hose extension 3. The aft housing segment 2 and the forward hose extension 3 are coaxial. They can be of unitary, one-piece construction or they can be assembled from parts which are secured to each other with any one of several connecting techniques such as by bonding. Housing 1 with its aft segment 2 and hose extension 3 is preferably made of a physiologically inert plastic material.

A puncturing needle 4 is axially movably disposed inside housing 1. The puncturing needle 4 extends over the full length of hose extension 3. An annular channel 5 is formed between the outer circumference of puncturing needle 4 and the inner circumference of hose extension 3.

Channel 5 terminates in a forward housing chamber 6 in aft housing segment 2. The end of the housing chamber facing away from the hose extension is formed by a conically converging, outer sealing section 7. A sealing body 8 surrounds the outer circumference of the puncturing needle and is located in the forward housing chamber 6. The aft end of the sealing body defines a conically shaped inner sealing section 9. The angles defined by the two conical sealing sections are substantially equal. FIG. 1 shows the outer sealing section 7 and the inner sealing section 9 axially spaced apart.

A bore 10 extends axially in a rearward direction; that is, away from hose extension 3, from the forward housing chamber 6. On its circumference, the axial bore 10 has thread grooves 11 with a steep thread angle. In the vicinity of axial bore 10, the outer circumference of the puncturing needle 4 has radially protruding threads which engage the thread grooves 11 and which have a thread angle equal to that of the thread grooves 11.

The aft end of housing 1 includes a blind bore 13 that is coaxial and in fluid communication with axial housing bore 10. The aft end of puncturing needle 4 projects past the axial bore 10 and into blind bore 13. In the area of the blind bore, a connector 16' is fluidly coupled to and sealingly extends about the aft end of the puncturing needle. The connecting piece 16' is part of the fluid withdrawal mechanism 14 of which, in FIG. 1, only a three-way valve 15 is additionally shown.

The three-way valve 15 has an intake 16 and the aft end of needle 4 is sealingly coupled and non-rotationally secured to the intake. The three-way valve further has a first outlet 17 at a right angle to the axial direction of housing 1. A second outlet 18 is substantially coaxial with the axis of housing 1. The three-way valve 15 has on its inside a known valve body 19 which can be switched between a first position, in which intake 16 is coupled to first outlet 17, and a second position, in which the first outlet is coupled to the second outlet 18. A collection container (not shown) is fluidly connected to the second outlet 18 by a hose (not shown) in a manner well known to those of skill in the art. The first outlet 17 is constructed so that a syringe or pump (not shown) can be attached to it.

Housing segment 2 further has a sight window 20 in the area of the forward housing chamber 6. The sight window permits one to view the forward housing chamber 6 from the exterior.

FIG. 1 shows the puncturing set in a position in which the pointed end 21 of the puncturing needle projects from the forward free end of hose extension 3.

Figure 2:
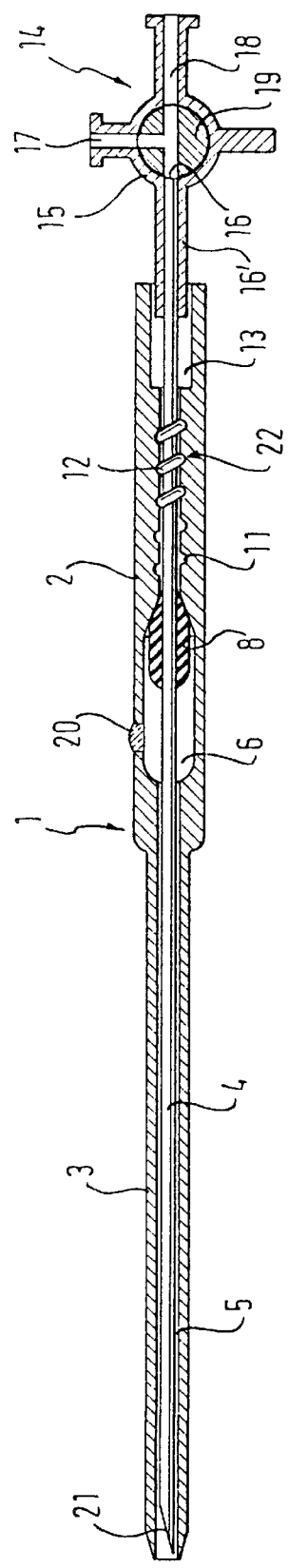
FIG. 2 illustrates the puncturing set shown in FIG. 1 with the needle in its retracted position.

FIG. 2 shows the same puncturing set as FIG. 1 but with needle 4 in its retracted position in which its pointed end 21 is disposed within hose extension 3. To place the needle in this position, three-way valve 15 is axially moved from its forward position, shown in FIG. 1, to its rearwardly retracted position, shown in FIG. 2, by turning thread connection 22, formed by thread grooves 11 and projecting threads 12, to translate the rotary motion into an axial movement of the needle. As the needle is threaded in a rearward direction, sealing body 8 moves with the needle rearwardly to engage the inner and outer sealing sections 7, 9 and form a seal between them.

Figure 3:
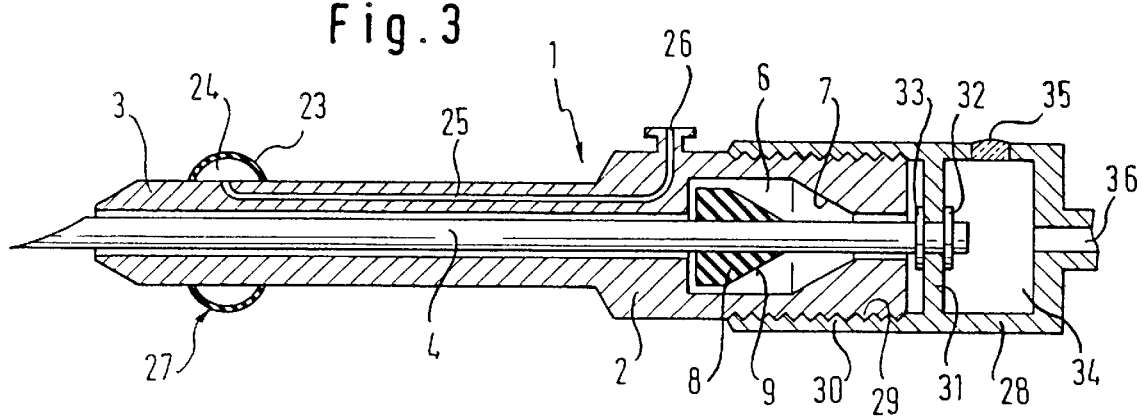
FIG. 3 shows a modified seal and a drive mechanism for the puncturing needle made in accordance with an alternative embodiment of the invention.

FIG. 3 shows an alternative embodiment of the puncturing set of the present invention which has a larger diameter and a lesser length. In the example shown in FIG. 3, as well as the examples shown in the succeeding figures, like parts are given the same reference numerals as were used in the example shown in FIGS. 1 and 2.

A radially expandable wall segment 23 is provided in the vicinity of the forward end of hose extension 3. It may, for example, be constructed of rubber or another flexible and elastic material. The flexible wall segment 23 surrounds an inner space 24 that circumvents the hose extension. It is in fluid communication with a pressure connection 26 in aft housing segment 2 via a pressure channel 25 in the wall of hose extension 3. Pressurized air or inert gas can be directed through connection 26 and channel 5 into inner space 24, which causes the flexible wall segment 23 and the inner space 24 to inflate into a balloon-like annular expansion about the outer side of hose extension 3. The annular expansion 27 prevents the puncturing set from unintentionally sliding out of the body.

The aft end of the puncturing set in FIG. 3 has a cap 28 with an inner thread 29 in engagement with an outer thread 30 on an aft end of the aft housing segment 2. A cross wall 31 extends at right angle to the axis of puncturing needle 4 across the inside of cap 28. The aft end of puncturing needle 4 is at least axially immovably secured thereto in a yoke-like fashion. Retainer rings 32, 33 are located on the rearwardly and forwardly facing sides, respectively, of cross wall 31 and clamp the puncturing needle 4 against axial motion. Accordingly, puncturing needle 4 can be moved between its limiting positions by turning cap 28.

The aft portion of cap 28 forms a hollow space 34 which is in fluid communication with the aft end of puncturing needle 4. A sight window 35 is formed at an appropriate location in the wall of cap 28 which defines the hollow space 34.

The aft end of cap 28 has an outlet channel 36 which is in fluid communication with hollow space 34. The outlet channel can also be in fluid communication with a three-way valve 15 that is formed as a part of cap 28 shown in FIG. 3.

Figure 4:
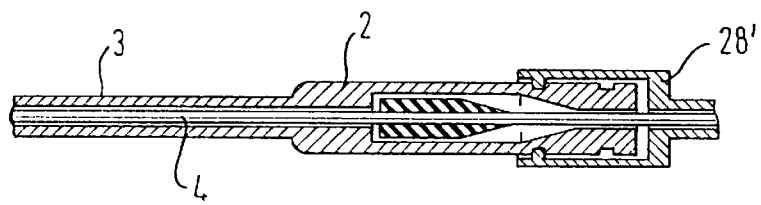
FIG. 4 shows another embodiment of the actuating mechanism for the needle.

FIG. 4 schematically illustrates an alternative to the puncturing set shown in FIG. 3. Puncturing needle 4 is axially fixed with respect to a cap 28' in a manner similar to that in which the needle is axially fixed to yoke-like cross wall 31 of cap 28 shown in FIG. 3. However, cap 28 is not threadably attached to the aft housing segment 2. In its place a ratchet mechanism permits axial movement of cap 28 (together with puncturing needle 4) between two terminal positions at which ratchets lock. For example, the outer periphery of aft housing segment 2 can be shaped so that the ratchet element of cap 28' can engage it. As an alternative to the just-described axial motion mechanism, the ratchet mechanism can also be constructed as a rotary mechanism. In such a case, the ratchet element on cap 28' engages and moves along a screw-like track on the outer surface of the aft housing segment. Ends of the track define ratchet elements which engage and thereby releasably lock the cap 28' in its terminal positions.

Figure 5:
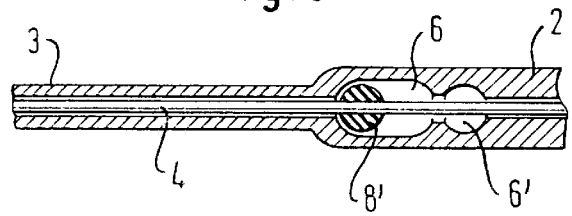
FIG. 5 shows a further embodiment of a seal for the puncturing needle.

Another embodiment is illustrated in FIG. 5. The puncturing needle 4 is surrounded by a spherically shaped sealing body 8'. It is preferably constructed of an elastic material, as is true for sealing body 8. An aft housing chamber 6' is formed in aft housing segment 2 and communicates with the forward housing chamber 6 through an opening which has a diameter that is slightly smaller than the outer diameter of spherical sealing body 8'. The sealing body can be moved from the forward housing chamber 6 into the aft housing chamber 6' by resiliently deforming the constriction between the two chambers. The aft housing chamber 6' is also spherical, or at least partially spherical, so that it can receive the spherically shaped sealing body 8' and form a seal when the puncturing needle 4 is in its retracted position.

Figure 6:
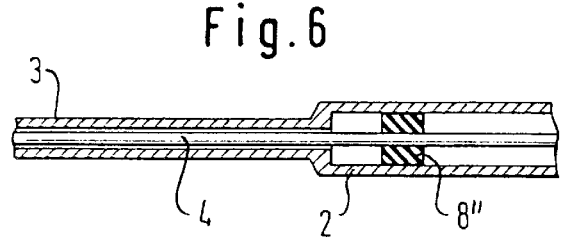
FIG. 6 shows a still further embodiment of the seal for the puncturing needle.

A particularly simple alternative construction for the seal is shown in FIG. 6. A radial seal 8" in the form of an O-ring or a packing, as is well known, establishes a seal between the inner diameter of aft housing segment 2 and the circumference of puncturing needle 4.

Figure 7:
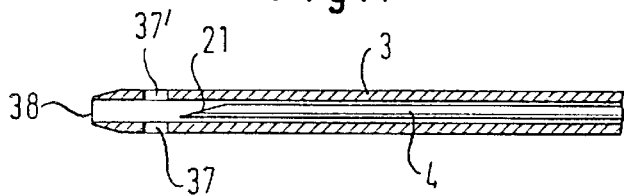
FIG. 7 is another embodiment of the present invention in the form of an alternative construction of a forward end thereof.

FIG. 7 illustrates an alternative embodiment for the forward end of hose extension 3. The free end of the hose extension has lateral openings 37, 37' that extend through the wall of the hose in a vicinity of the free end thereof. The lateral openings 37, 37' permit a liquid flow into the hose extension 3 and the interior of puncturing needle 4 when the opening 38 at the free end of the hose extension becomes plugged.

The process of puncturing is described by reference to FIGS. 1 and 2. Puncturing needle 4 is initially moved into the extended position shown in FIG. 1 in which the pointed end 21 of the needle projects from the end of hose extension 3. The puncturing set is then advanced through the body wall into the body cavity. In the process, the pointed end 21 of the puncturing needle and a portion of the hose extension 3 also enter the body. As soon as the flow of body fluid into the forward housing chamber 6 becomes visible through side window 20, a judgment can be made if the desired point in the body cavity has been reached. Thereafter, the puncturing needle 4 is retracted into the position shown in FIG. 2 in which the pointed end 21 of the needle is completely inside hose extension 3. The puncturing needle 4 stabilizes the hose extension made of plastic and prevents its pinching. At the same time, the pointed needle end is prevented from causing undesired damage to tissue walls surrounding the body cavity. When available, the annular expansion 27 shown in FIG. 3 is inflated so that, upon a slight retraction of the puncturing set, the annular expansion prevents the puncturing set from further sliding out of the body tissue. The body fluid that is to be removed can now flow under the prevailing pressure to the collection container. The flow of body fluid can be from the interior of the puncturing needle into the fluid withdrawal mechanism 14, or into a syringe attached to first outlet 17 of three-way valve 15. By switching the three-way valve, the fluid can then flow through the second outlet 18 into the collection container. Following the withdrawal of the desired amount of body fluid from the body cavity, the annular expansion 27 is deflated and the puncturing set is retracted from the body.

What is claimed is:

1. A puncturing set comprising:
   a housing including a hose extension having a free end;
   a tubular puncturing needle disposed in the housing and extending axially substantially through the hose extension, the puncturing needle having a forward upstream pointed end, the puncturing needle being axially movable between an extended position and a retracted position, the pointed end of the puncturing needle extending axially past the free end and disposed outside of the hose extension in the extended position and being disposed inside the hose extension in the retracted position;

a locking mechanism for locking the puncturing needle in the retracted position;

a fluid withdrawal mechanism arranged at an aft downstream end of the puncturing needle; and a sealing arrangement for sealing a space between the puncturing needle and the housing at least when the puncturing needle is in the retracted position.

2. A puncturing set according to claim 1 wherein the sealing arrangement comprises a radial seal disposed between the outer surface of the puncturing needle and the inner surface of the housing.

3. A puncturing set according to claim 1 wherein the puncturing needle is movably coupled with the housing via a threaded connection.

4. A puncturing set according to claim 3 wherein the threaded connection has a steep thread pitch.

5. A puncturing set according to claim 1 wherein the sealing arrangement comprises a seal disposed on the periphery of the puncturing needle and having an inner sealing section; and an outer sealing section formed in the interior of the housing, the inner and outer sealing sections being axially spaced from one another when the puncturing needle is in the extended position and being in sealing contact with one another when the puncturing needle is in the retracted position.

6. A puncturing set according to claim 5 wherein the inner sealing section includes a surface angularly inclined relative to the axis of the puncturing needle and conically surrounding the periphery of the puncturing needle, and wherein the outer sealing section includes an inwardly facing conical surface in the housing.

7. A puncturing set according to claim 5 wherein the inner sealing section includes a spherical surface surrounding the periphery of the puncturing needle, and wherein the outer sealing section includes a partially spherically shaped inner surface of a hollow space in the housing.

\* \* \* \* \*